United States Patent
Kojima et al.

(10) Patent No.: US 6,783,966 B1
(45) Date of Patent: Aug. 31, 2004

(54) ALPHA1, 4-GALACTOSYLTRANSFERASE AND DNA ENCODING THEREOF

(75) Inventors: Yoshinao Kojima, Kariya (JP); Satoshi Fukumoto, Nishisonogi-gun (JP); Keiko Furukawa, Nagoya (JP); Tetsuya Okajima, Nagoya (JP); Koichi Furukawa, Nagoya (JP)

(73) Assignee: Seikagaku Corporation, Tokyo (JP)

( * ) Notice: Subject to any disclaimer, the term of this patent is extended or adjusted under 35 U.S.C. 154(b) by 166 days.

(21) Appl. No.: 09/641,701

(22) Filed: Aug. 21, 2000

(30) Foreign Application Priority Data

Feb. 14, 2000 (JP) ........................ 2000-035454

(51) Int. Cl.$^7$ ............................ C12N 15/54; C12N 9/10
(52) U.S. Cl. .................... 435/193; 435/320.1; 435/325; 435/252.3; 536/23.2
(58) Field of Search .............................. 435/193, 320.1, 435/325, 252.3; 536/232

(56) References Cited

U.S. PATENT DOCUMENTS

| | | | | |
|---|---|---|---|---|
| 5,625,048 A | * | 4/1997 | Tsien et al. | ................. 536/23.4 |
| 2003/0138807 A1 | * | 7/2003 | Clausen et al. | ................. 435/6 |

FOREIGN PATENT DOCUMENTS

| | | | |
|---|---|---|---|
| WO | 01/57190 | * | 2/2000 |

OTHER PUBLICATIONS

Liu et al. GenBank Accesion No. AB041418. (Apr. 2000).*
McClaren. GenBank Accesion No. Z82176. (Dec. 1999).*
Y. Kojima, et al., The Japanese Biochemical Society, vol. 71, No. 8, pp. 704 and 1118, "2P–008 Expression Cloning and Analysis of Human CD77 Synthase(α 1,4–Galactosyltransferase) Gene", Aug. 25, 1999 (with English translation).
Y. Kojima, et al., The Journal of Biochemical Chemistry, vol. 275, No. 20, pp. 15152–15156, Molecular Cloning of Globotriaosylceramide/CD77 Synthase, A Glycosyltransferase That Initiates the Synthesis of Globo Series Glycosphingolipids:, May 19, 2000.
R. Steffensen, et al., The Journal of Biological Chemistry, vol. 275, No. 22, pp. 16723–16729, "Cloning and Expression of the Histo–Blood Group $P^K$ UDP–Galactose: Galβ1–4Glcβ1–Cer α1,4–Galactosyltransferase", Jun. 2, 2000.
N. Taniguchi, et al., The Journal of Biological Chemistry, vol. 260, No. 8, pp. 4908–4913, "Purification and Properties of Rat Liver Globotriaosylceramide Synthase, UDP–Galactose:Lactosylceramide α1–4–Galactosyltransferase", Apr. 25, 1985.

S. Pal, et al., Journal of Lipid Research, vol. 33, pp. 411–417, "UDP–Galactose:Globotriaosylceramide α–Galactosyltransfease Activity in Rat Pheochromocytoma (PC12h) Cells", 1992.
M. Mobassaleh, et al., Am. J. Physiol. 267, pp. G618–G624, "Developmentally Regulated $Gb_3$ Galactosyltransferase and α–Galactosidase Determine Shiga Toxin Receptors in Intestine", 1994.
S. Taga, et al., Biochimica et Biophysica Acta 1254, pp. 56–65, "Sequential Changes in Glycolipid Expression During Human B Cell Differentiation: Enzymatic Bases", 1995.
J. Wiels, et al., The Journal of Biological Chemistry, vol. 259, No. 23, pp. 14783–14787, "Enzymatic and Organizational Difference in Expression of a Burkitt Lymphoma–Associated Antigen (Globotriaosylceramide) in Burkitt Lymphoma and Lymphoblastoid Cell Lines", Dec. 10, 1984.
S. Taga, et al., Int. J. Cancer:61, pp. 261–267, "Differential Regulation of Glycosphingolipid Biosynthesis in Phenotypically Distinct Burkitt's Lymphoma Cell Lines", 1995.
A. Pudymaitis, et al., Archives of Biochemistry and Biophysics, vol. 286, No. 2, pp. 448–452, "Verotoxin–Resistant Cell Clones are Deficient in the Glycopliid Globotriosylceramide: Differential Basis of Phenotype", May 1, 1991.
M. Mobassaleh, et al., Analytical Biochemistry 214, pp. 295–300, "A Quantitative Immunostaining Method for the Measurement of UDP–Galactose: Lactosylceramide Galactosyltransferase for the Synthesis of Globotriaosylceramide in Rabbit Small Intestine and HeLa Cells[1]", 1993.

* cited by examiner

Primary Examiner—Rebecca Prouty
(74) Attorney, Agent, or Firm—Oblon, Spivak, McClelland, Maier & Neustadt, P.C.

(57) ABSTRACT

The object of the present invention is to provide α1,4-galactosyltransferase to transfer a galactose residue to C4 position of galactose residue of lactosylceramide or galactosylceramide, and DNA coding for the enzyme.

What is provided includes the following polypeptides (a) and (b), and DNAs encoding thereof:
  (a) a polypeptide consisting of an amino acid sequence represented by the amino acid Nos. 46-353 in SEQ ID NO: 2; or
  (b) a polypeptide which comprises an amino acid sequence including substitution, deletion, insertion or transposition of one or few amino acids in the amino acid sequence of (a) and which has an enzymatic activity to transfer a galactose residue from a galactose donor to C4 position of galactose residue of lactosylceramide or galactosylceramide which serves as an acceptor.

4 Claims, 9 Drawing Sheets

ALPHA1, 4-GALACTOSYLTRANSFERASE AND DNA ENCODING THEREOF

BACKGROUND OF THE INVENTION

1. Field of the Invention

The present invention relates to the production of a polypeptide using a recombinant DNA, or to a tool useful for diagnosis or treatment of diseases, or more specifically to α1,4-galactosyltransferase and DNA encoding thereof, a recombination vector containing the DNA, and a transformed cell transfected with the DNA or by the recombination vector, and to a method for producing Gb3/CD77 or globo-series glycolipids by using the transformed cell.

2. Description of the Related Art

Glycosphingolipids are amphipathic molecules(ref.1) that are synthesized by sequential actions of glycosyltransferases (ref.2). Addition of one of three different sugars onto lactosylceramide (which may be termed "LacCer" hereinafter) results in the synthesis of either one of three major glycolipid series, i.e., ganglioside-series (α2,3-sialic acid), lacto/neolacto-series (β1,4-N-acetylglucosamine) and globo-series (α1,4-galactose). Although a number of genes coding for enzymes responsible for the synthesis of the carbohydrate moiety of glycosphingolipids have been recently isolated(ref.3), no glycosyltransferase genes specific for the synthesis of globo-series glycolipids have been isolated to date.

Globotriaosylceramide (hereinafter sometimes referred to as "Gb3") is synthesized by α1,4-galactosyltransferase (α1,4 Gal-T) from LacCer(ref.4). This glycolipid has been characterized on red blood cells as the $P^k$ antigen of the P blood group system(ref.5). Since Wiels et al(ref.6) reported that Gb3 was a Burkitt's lymphoma associated antigen, the expression and biological significance of Gb3 have been vigorously studied(ref.7, 8 and 9). Since Gb3 was clustered as CD77, this antigen will be referred to as Gb3/CD77.

Gb3/CD77 was reported to be expressed in high amounts on Burkitt's lymphoma cells. However, it is now considered to be a differentiation antigen expressed on B cells, and can also be found in some malignant tumors of B cell lineage (ref.7). Among normal leukocytes, it is only expressed on a subset of tonsillar B cells in the germinal centers (GC) (ref.9). Interestingly, GC B lymphocytes expressing Gb3/CD77 undergo rapid and spontaneous apoptosis when isolated and cultured in vitro(ref.11). Furthermore, Burkitt's lymphoma cells with Gb3/CD77 antigen were also easily induced to enter apoptosis upon culture at low serum concentration or cross-linking by anti-immunoglobulin M antibodies(ref.12).

Gb3/CD77 has been recognized as a receptor for verotoxins (VTs), the Shiga-like toxin from *E. coli* O157 strain that can trigger serious cytotoxic effects(ref.13 and 14). VT B-subunit specifically binds to Gb3/CD77, then A subunit is incorporated into cells, resulting in the degradation of 28 S ribosomal RNA and cell death(ref.15). However, only B-subunit is also able to induce apoptosis when cross-linked (ref.16). These results indicate that Gb3/CD77 is a critical molecule in mediating apoptosis signals, although the precise mechanisms remain to be investigated.

As stated above, it was revealed that Gb3/CD77, a globo-series glycolipid, is syntheized by addition of α1,4-galactose to LacCer(ref.4), but the glycosyltransferase specific for this synethetic reaction has not been isolated yet. An object of the present invention is to isolate a Gb3/CD77 synthase, that is, α1,4-galactosyltransferase, and DNA encoding thereof, and to provide the use thereof.

The present inventors have studied hard to achieve the above objects, and succeeded in isolating DNA encoding α1,4-galactosyltransferase, revealing its nucleotide sequence, and confirming that the DNA is responsible for the expression of active α1,4-galactosyltransferase. Thus, they achieved the present invention.

SUMMARY OF THE INVENTION

The present invention provides a polypeptide of (a) or (b) below (hereinafter sometimes referred to as "the polypeptide of the present invention"):

(a) a polypeptide consisting of an amino acid sequence represented by the amino acid Nos. 46–353 in SEQ ID NO: 2; or (b) a polypeptide which comprises an amino acid sequence including substitution, deletion, insertion or transposition of one or few amino acids in the amino acid sequence of (a) and which has an enzymatic activity to transfer a galactose residue from a galactose donor to C4 position of galactose residue of lactosylceramide or galactosylceramide which serves as an acceptor.

The polypeptide of the present invention also includes a polypeptide of(a') or (b') below:

(a') a polypeptide consisting of an amino acid sequence represented by the amino acid Nos. 20–353 in SEQ ID NO:2; or (b') a polypeptide which comprises an amino acid sequence including substitution, deletion, insertion or transposition of one or few amino acids in the amino acid sequence of (a') and which has an enzymatic activity to transfer a galactose residue from a galactose donor to C4 position of galactose residue of lactosylceramide or galactosylceramide which serves as an acceptor.

The polypeptide of the present invention also includes a polypeptide of (a") or (b") below:

(a") a polypeptide consisting of an amino acid sequence represented by SEQ ID NO:2; or (b") a polypeptide which comprises an amino acid sequence including substitution, deletion, insertion or transposition of one or few amino acids in the amino acid sequence of (a") and which has an enzymatic activity to transfer a galactose residue from a galactose donor to C4 position of galactose residue of lactosylceramide or galactosylceramide which serves as an acceptor.

The present invention also provides a DNA encoding the polypeptides according to any one of above polypeptides (hereinafter sometimes referred to as "the DNA of the present invention"). The DNA of the present invention includes a DNA represented by (a) or (b) below:

(a) a DNA comprising a nucleotide sequence represented by nucleotide Nos. 269 to 1192 in SEQ ID NO:1; or (b) a DNA hybridizable with a DNA comprising a nucleotide sequence represented by SEQ ID NO:1, a nucleotide sequence complimentary to SEQ ID NO:1, or a part of those sequences, under a stringent condition.

The DNA of the present invention also includes a DNA encoding a polypeptide having an enzymatic activity to transfer a galactose residue from a galactose donor to C4 position of galactose residue of lactosylceramide or galactosylceramide which serves as an acceptor.

The present invention still further provides a recombination vector containing the DNA of the present invention.

The present invention still further provides a transformed cell obtained by transfecting a host cell with the DNA of the present invention or the recombination vector.

The present invention still further provides a method for producing the polypeptide of the present invention, comprising the steps of:
 producing the polypeptide of the present invention by culturing the transformed cell above in a medium; and
 recovering said polypeptide from the medium and/or a cell extract of the cultured transformed cell.

10. The present invention still further provides a method for producing Gb/CD77 comprising the steps of:
 exposing the polypeptide according to any one of claims 1 to 3, or a cultured product of the transformed cell according to claim 8, to lactosylceramide, to cause thereby enzymatic reaction; and recovering Gb3/CD77.

The present invention still further provides a method for producing a glycolipid as represented by the following formula (1) comprising the steps of:
 exposing the polypeptide of the present invention, or a cultured product of the transformed cell above, to galactosylceramide, to cause thereby enzymatic reaction; and
 recovering the glycolipid represented by the following formula (1):

Galα1→4Gal-Cer    (1)

wherein Gal represents a galactose residue, Cer represents a ceramide residue and α1→4 represents an α1-4 glycosidic linkage.

In the present invention, the enzyme having an activity to transfer a galactose residue from a galactose donor to C4 position of galactose residue of lactosylceramide or galactosylceramide which serves as an acceptor, will be called "α1,4-galactosyltransferase." Further, the activity of the enzyme to transfer a galactose residue from a galactose donor to C4 position of galactose residue of lactosylceramide or galactosylceramide which serves as an acceptor, will be called "α1,4-galactosyltransferase activity."

A: TLC of glycolipids extracted from L cells transfected with pCDM8 (VC) or pVTR1/CDM8 (TF). RBC represents neutral glycolipids extracted from human B red blood cells.

B: TLC immunostaining of Gb3/CD77 by mAb38.13.

Figure 3:
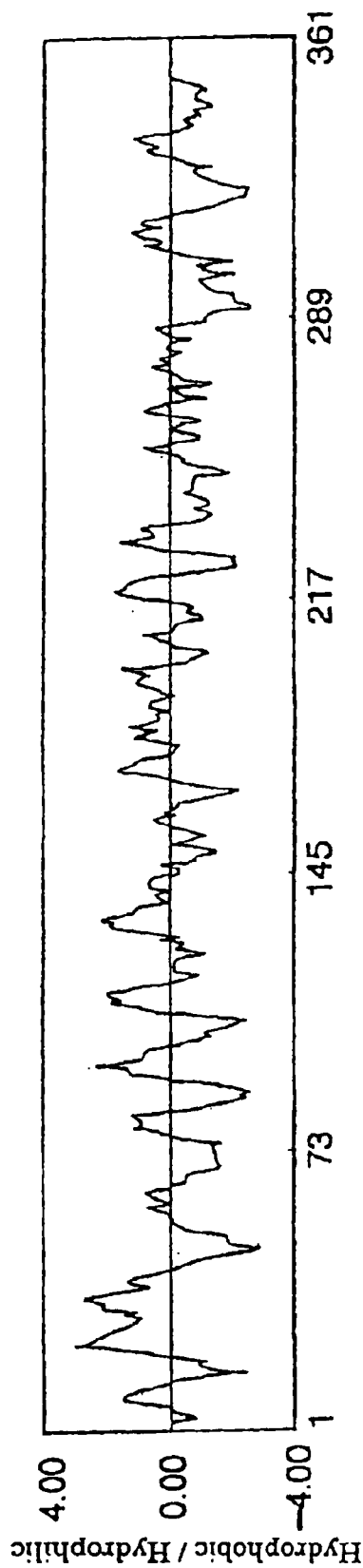

FIG. 3 shows the hydropathy plot of a polypeptide of the present invention.

Figure 4:
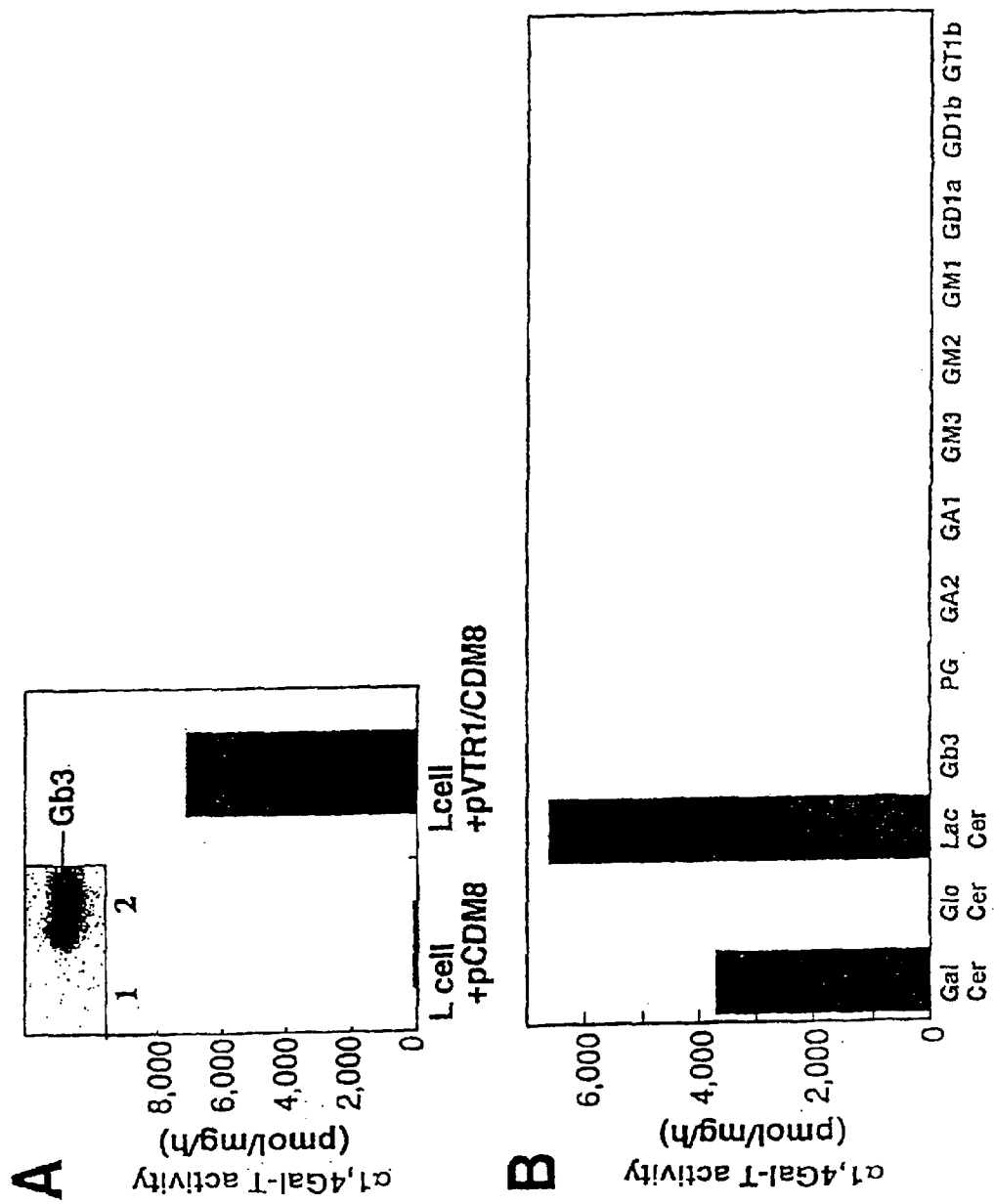

FIG. 4 shows the α1,4 Gal-T activity in the extracts of transient transfectants of pVTR1.

A: α1,4 Gal-T activity when LacCer was used as an acceptor.

B: α1,4 Gal-T activity when various acceptors were used. PG represents paragloboside.

Figure 5:
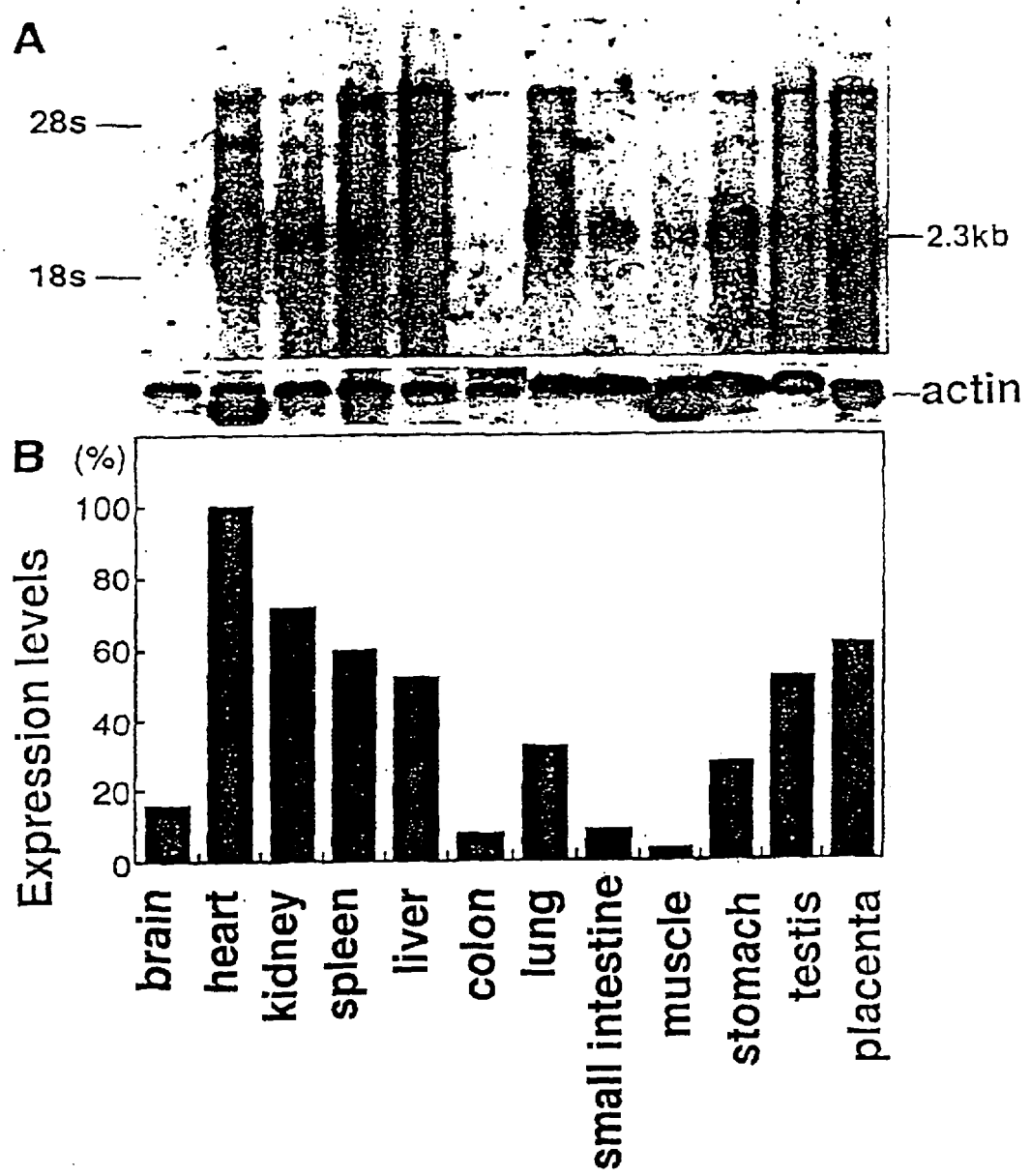

FIG. 5 shows the result of northern blotting of α1,4 Gal-T gene.

A: the upper columns show the results of hybridization with a $^{32}$P-labeled probe derived from pVTR1, while the lower columns show the results of hybridization of the same membranes as in A with a β-actin cDNA probe(control).

B: the expression levels of mRNA of α1,4 Gal-T gene were compared among various human tissues. The ordinate represents the percentage of the expression level of a given tissue with respect to the level of heart after correction with the control.

Figure 6:
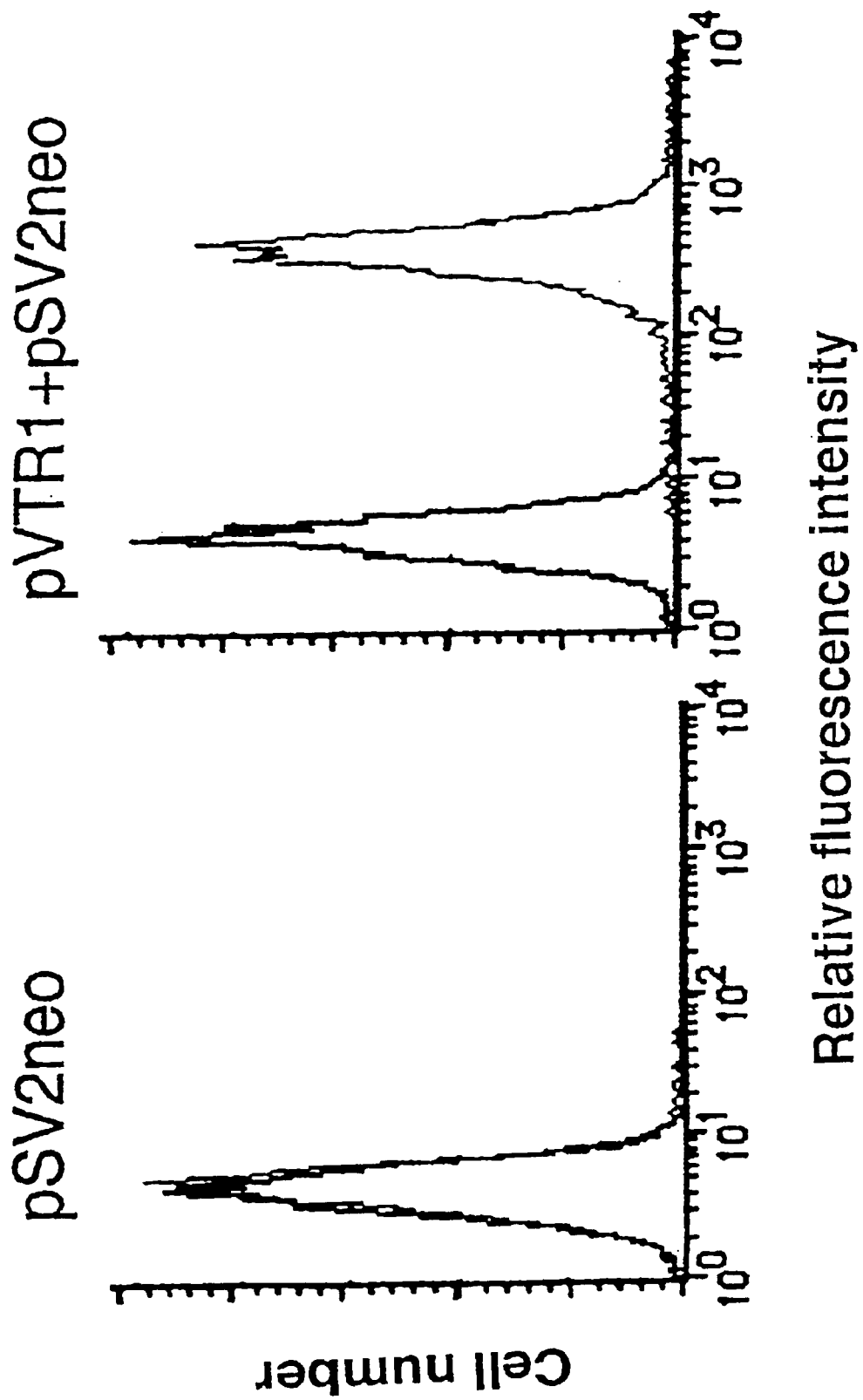

FIG. 6 shows flowcytometry of stable transfectant cells. The left diagram relates to cells transfected with pSV2neo while the right diagram to cells transfected with pVTR1 and pSV2neo. The thin line indicates the number of cells stained with mAb38.13 and FITC-conjugated rabbit anti-rat IgG (secondary antibodies) while the thick line the number of cells stained only with the secondary antibodies (control).

Figure 7:
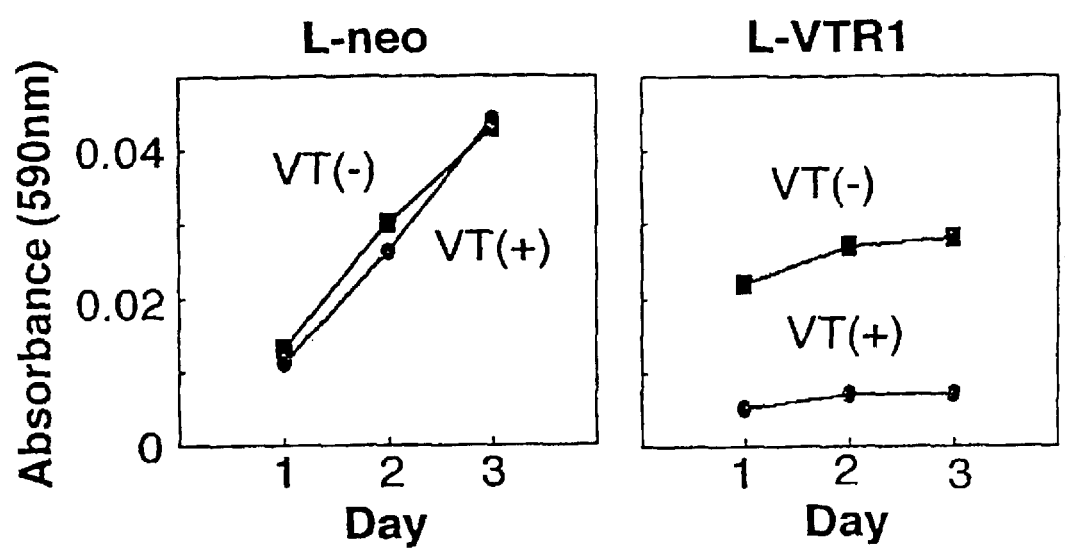

FIG. 7 shows the results of MTT assay of L-neo and L-VTR1. The left graph shows the result of L-neo while the right one the result of L-VTR1.

Figure 8:
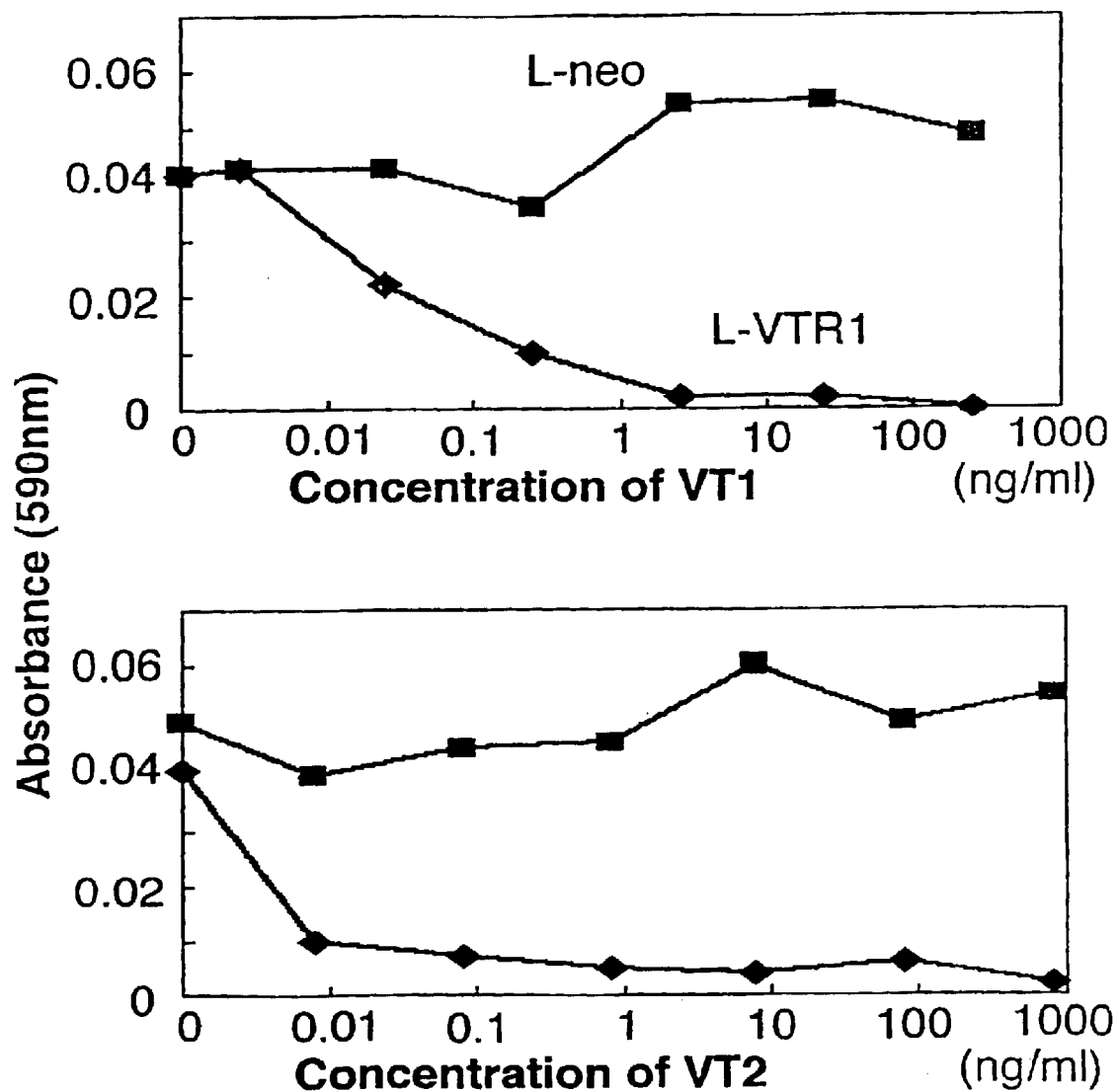

FIG. 8 shows the effect of vero toxins on the cell growth.

Figure 9:
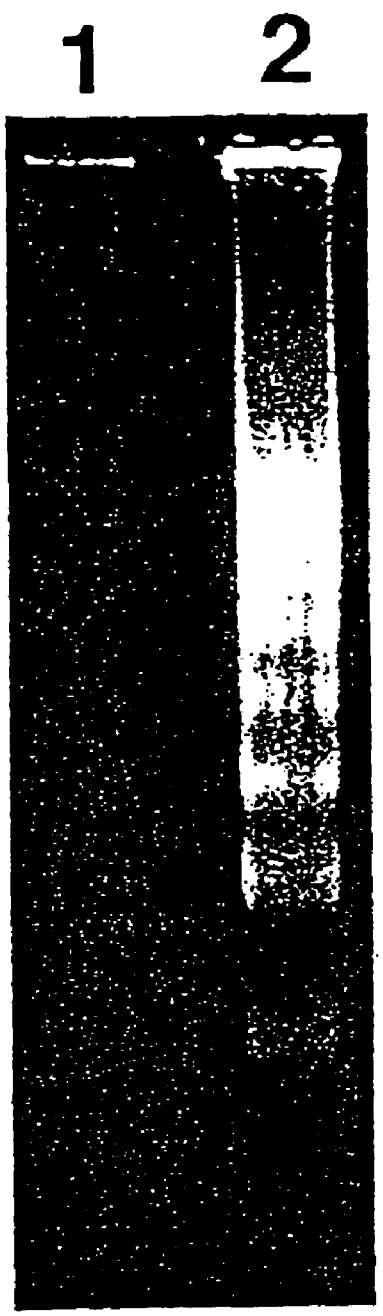

FIG. 9 shows an electrophoresis indicating the result of DNA fragmentation assay.

DESCRIPTION OF THE PREFERRED EMBODIMENTS

The mode for carrying out the present invention is described below.

<1> The Polypeptide of the Present Invention

The polypeptide of the present invention is a polypeptide of (a) or (b) below:
 (a) a polypeptide consisting of an amino acid sequence represented by the amino acid Nos. 46–353 in SEQ ID NO: 2; or
 (b) a polypeptide which comprises an amino acid sequence including substitution, deletion, insertion or transposition of one or few amino acids in the amino acid sequence of (a) and which has an enzymatic activity to transfer a galactose residue from a galactose donor to C4 position of galactose residue of lactosylceramide or galactosylceramide which serves as an acceptor.

The above polypeptides contain at least a catalytic domain of α1,4-galactosyltransferase as will be described later. α1,4-galactosyltransferase comprises, in order from its N-terminal, a cytoplasmic domain, transmembrane domain, and catalytic domain. The polypeptides described above in (a') and (b') comprise at least the transmembrane and catalytic domains. The polypeptides described above in (a") and (b") comprise the cytoplasmic, transmembrane and catalytic domains. These peptides are all included in the polypeptides of the present invention.

An example of the amino acid sequence of a polypeptide of the present invention is represented in SEQ ID NO:2. In SEQ ID NO:2, amino acid Nos. 1–19 represents the cytoplasmic domain, Nos. 20–45 the transmembrane domain, and Nos. 46–353 the catalytic domain.

Among those polypeptides, the polypeptides (a), (a') and (a") are preferred; the polypeptides (a') and (a") are more preferred; and the polypeptide (a") is most preferred. However, any one of them may be used as long as it has an α1,4-galactosyltransferase activity.

In this specification, the term "a polypeptide which comprises an amino acid sequence including substitution, deletion, insertion or transposition of one or few amino acids and which has an enzymatic activity to transfer a galactose residue from a galactose donor to C4 position of galactose residue of lactosylceramide or galactosylceramide which serves as an acceptor" means that, one or more amino acid residues of the polypeptide may be substituted, deleted, inserted, or transferred as long as such modification does not substantially affect the ability to the enzymatic activity (α1,4 Galactosyltransferase activity) of the polypeptide to transfer a galactose residue from a galactose donor to C4 position of galactose residue of lactosylceramide or galactosylceramide which serves as an acceptor.

Mutation such as substitution, deletion, insertion, or transposition of amino acid residues may occur in the amino acid sequence of the polypeptides existing in nature due to, for example, the modifying reaction of the biosynthesized polypeptides in the living organisms or during their purification as well as polymorphism and mutation of the DNAs encoding the polypeptides, nevertheless some of mutated polypeptides are known to have substantially the same physiological and biological activities as the intact polypeptides that have not been mutated. The polypeptide of the present invention includes those having slightly different structures but not having a significant difference in the functions. The polypeptide of the present invention also includes those which have been artificially treated to have mutation as described above in the amino acid sequences. In this case, a further variety of mutants can be produced. For example, a polypeptide having a human interleukin 2 (IL-2) amino acid sequence, in which a cysteine residue has been replaced with a serine residue, is known to retain the interleukin 2 activities (Science 224, 1431 (1984)). Furthermore, a polypeptide of certain kind is known to have a peptide region that is not essential for exhibiting its activities. Examples of such polypeptides include a signal peptide contained in a polypeptide that is secreted extracellularly and a pro-sequence found in a precursor of protease, and the like. Most of these regions are removed after translation or upon conversion into an active form of the polypeptides. These polypeptides exist in different primary structures but finally have equivalent functions. Such polypeptides are also included in the polypeptide of the present invention.

The term "few amino acids" used herein means the number of amino acid residues that may be mutated to the extent that the enzymatic activities of the polypeptide of the present invention are not lost. For example, in a polypeptide consisting of 400 amino acid residues, about 2 to 20, preferably 2 to 10, more preferably 2 to 5 or less of amino acid residues may be mutated.

The α1,4-galactosyltransferase activity can be assayed by a known method(ref.4). Specifically, the assay consists of using UDP-galactose (UDP-Gal) as a donor, and depending on the reaction where galactose is transferred by the enzyme to LacCer(acceptor). From above, it is obvious that any one skilled in the art could easily select substitution, deletion, insertion or transposition of one or more amino acid residues which does not substantially affect the enzymatic activity, using its α1,4-galactosyltransferase activity as an index.

The polypeptide of the present invention was obtained as follows:

cDNA of α1,4-galactosyltransferase was isolated from human melanoma cell line; the cDNA was expressed in mouse fibroblasts; and the peptide was identified and characterized, and its structure was determined. The polypeptide of the present invention may be obtained by expressing the DNA of the present invention as described later, in appropriate cells. The same polypeptides chemically synthesized are naturally included in the present invention. The method for producing the polypeptide of the present invention using the DNA of the present invention will be described later.

The polypeptide of the present invention is not necessarily a single polypeptide but may be a part of a fusion protein if necessary. A fusion protein comprising the polypeptide of the present invention and another polypeptide such as protein A may be cited as such an example.

The polypeptide of the present invention may consist of a polypeptide alone, or contain a sugar chain or the like, as long as it has the enzymatic activity to transfer a galactose residue from a galactose donor to C4 position of galactose residue of lactosylceramide or galactosylceramide which serves as an acceptor.

<2> DNA of the Present Invention

The DNA of the present invention is a DNA encoding the polypeptide of the present invention as described above. The DNAs encoding the polypeptides described below in (a) and (b) may be cited as an example:

(a) a polypeptide consisting of an amino acid sequence represented by the amino acid Nos. 46–353 in SEQ ID NO: 2; or (b) a polypeptide which comprises an amino acid sequence including substitution, deletion, insertion or transposition of one or few amino acids in the amino acid sequence of (a) and which has an enzymatic activity to transfer a galactose residue from a galactose donor to C4 position of galactose residue of lactosylceramide or galactosylceramide which serves as an acceptor.

Among the DNAs, the one coding for polypeptide (a) is more preferred.

The DNA encodes at least the catalytic domain of α1,4-galactosyltransferase, but the DNA of the present invention also includes DNAs encoding, in addition to above, the polypeptides including a transmembrane domain and/or cytoplasmic domain.

The DNA encoding the polypeptide (a) includes, for example, a DNA containing a nucleotide sequence represented by nucleotide Nos. 269–1192 in SEQ ID NO:1. The DNA encoding the polypeptide containing the transmembrane domain includes, for example, a DNA containing a nucleotide sequence represented by nucleotide Nos. 191–1192 in SEQ ID NO:1. The DNA encoding the polypeptide containing the cytoplasmic domain includes, for example, a DNA containing a nucleotide sequence represented by nucleotide Nos. 134–1192 in SEQ ID NO:1.

Furthermore the DNA comprising a nucleotide sequence represented by SEQ ID NO:1 has been derived from human originally. As a matter of course, however, the DNA of the present invention is not limited to any source, and includes those that are produced by genetic engineering procedure or chemical synthesis.

Furthermore, any one ordinarily skilled in the art would readily understand that the DNA of the present invention includes DNAs having nucleotide sequences different from what is described above due to degeneracy of the genetic codes.

The DNA of the present invention also includes DNA or RNA complementary to the DNA of the present invention. Furthermore, the DNA of the present invention may be either a single-stranded coding chain encoding the polypeptide of the present invention or a double-stranded chain consisting of the above single-stranded chain and a DNA or an RNA having a complementary nucleotide sequence thereto.

The DNA of the present invention was obtained by expression cloning as will be described later. However, since the nucleotide sequence of the DNA of the present invention was determined, it will be possible to isolate the same DNA from human-derived mRNA or cDNA, or a chromosomal DNA through PCR with an oligonucleotide prepared from the nucleotide sequence thus determined to serve as a primer, or from a cDNA library or chromosomal DNA library through hybridization with an oligonucleotide prepared from the nucleotide sequence thus determined to serve as a probe.

The gene encoding the polypeptide of the present invention derived from a chromosome is expected to contain introns in the coding region. DNA fragments separated by introns are also included in the DNA of the present invention.

The DNA of the present invention may include DNAs, as long as they code for the polypeptides having an enzymatic activity to transfer a galactose residue from a galactose donor to C4 position of galactose residue of lactosylceramide or galactosylceramide which serves as an acceptor, hybridizable with a probe comprising a nucleotide sequence complimentary to the nucleotide sequence of SEQ. ID No:1, or to a nucleotide sequence represented by nucleotide Nos. 269–1292, nucleotide sequence represented by nucleotide Nos. 191–1292, or nucleotide sequence represented by nucleotide Nos. 134–1292 of SEQ ID No:1, or with a probe comprising a part of those nucleotide sequences, under a stringent condition. The "stringent condition" here refers to a condition under which a so-called specific hybrid is formed, but no non-specific hybrids are formed (see Sambrook, J. et al., Molecular Cloning A Laboratory Manual, Second Edition, Cold Spring Harbor Laboratory Press (1989)). The "stringent condition" may include for example subjecting a test DNA to a solution containing 50% formamide, 4×SSC, 50 mM HEPES(pH 7.0), 10×Denhardt's solution, and 100 $\mu$g/ml of sermon sperm DNA, allowing it to hybridize in the solution at 42° C., and washing the yield in 2×SSC and 0.1% SDS solution at room temperature, then in 0.1×SSC and 0.1% SDS solution at a temperature of 50° C. or less.

Production of the polypeptide of the present invention may be achieved by cultivating transformed cells transfected with the DNA of the present invention on appropriate growth medium, thereby allowing the polypeptide of the present invention encoded by the DNA of the present invention to express itself, and by recovering the polypeptide thus expressed. The thus expressed polypeptide of the present invention can be extracted from a cultured product of the transformed cells (comprising both transformed cells and medium). However, if the polypeptide of the present invention is accumulated in the cytoplasm of transformed cells, or their membrane fraction, the polypeptide must be extracted from the transformed cells. Or, if the polypeptide is accumulated in medium, it must be extracted from medium. Or, if use of the transformed cells in which the polypeptide is expressed is desired, the transformed cells themselves, or their processed products may be used intact, or after they have been bound to an appropriate solid phase, or covered with gel for solidification. The "transformed cell" includes not only transformed cell themselves but also extracts from them.

For the transfection of the DNA of the present invention into a host cell, it is only necessary to prepare a recombination vector by inserting the DNA of the present invention into an appropriate vector, and to introduce the DNA of the present invention into a host cell through the recombination vector. The vector is preferably an expression vector.

The host cell is not limited to any specific cells, as long as they can fully play the function of the DNA of the present invention, or of the recombination vector containing the DNA of the present invention. Thus, it may include any animal cells, plant cells, micro-organisms (bacteria), or the like. Procaryotic cells such as E. coli, or eucaryotic cells such as mammalian cells may be exemplified. When a procaryotic cell such as E. coli is used, addition of sugar chain does not occur to the polypeptide produced as by expression of the DNA of the present invention, then the polypeptide of the present invention having no sugar chain can be obtained. When eucaryotic cell such as a mammalian cell is used, sugar chain may add to the polypeptide produced by expression of the DNA of the present invention, then the form of the polypeptide of the present invention comprising sugar chain can be obtained.

Specifically, the host cell to transfect with the DNA of the present invention may include for example L cells derived from mouse fibroblasts. Specifically, the vector may include pCDM8 or pcDNA3 expression vector (both available from Invitrogen). The culture medium and condition may be chosen appropriately according to a given host cell.

The DNA of the present invention may be expressed directly. Alternatively, it may be expressed with another polypeptide as a fusion polypeptide. The full-length DNA of the present invention may be expressed. It may also be expressed in part as a partial peptide.

The method for introducing the DNA of the present invention may depend on transfection based for example on DEAE-dextran method.

Recovering the polypeptide of the present invention from a cultured product may be performed by known extraction and purification methods for polypeptides. The cultured product used herein includes the medium and the cells in the medium.

Extraction of the polypeptide of the present invention may be performed, for example, by a method using a nitrogen cavitation apparatus, extraction from the cells disrupted by homogenization, glass bead milling, sonic wave treatment, osmotic shock, freeze-thawing procedure or the like, extraction by using detergent, or combination of those methods.

When the DNA of the present invention encoding the polypeptide (a") is expressed in L cells, the polypeptide of the present invention is localized at the membrane fraction of the cell. When the DNA of the present invention is expressed as a fusion protein comprising a polypeptide of the present invention (or a part thereof), and another peptide, so as to be a soluble protein, that fusion protein may be present in the cytoplasm. When the DNA of the present invention is expressed as a fusion protein comprising the polypeptide of the present invention or a part thereof and a secretion signal, the resulting protein may be secreted into medium. Isolation of DNA encoding a part of the polypeptide of the present invention may be achieved by preparing a primer previously designed to produce such a DNA, and applying the primer in PCR to human derived mRNA, cDNA library, or chromosomal DNA.

Specific examples of the method of purifying the polypeptide of the present invention extracted from the cells or medium include salting out with salt such as ammonium sulfate or sodium sulfate, centrifugation, dialysis, ultrafiltration, absorption chromatography, ion exchange chromatography, hydrophobic chromatography, reverse phase chromatography, gel filtration, gel permeation chromatography, affinity chromatography, electrophoresis, and any combination thereof.

It can be confirmed whether the polypeptide of the present invention has been produced or not by analyzing amino acid sequence, action, and substrate specificity of the purified polypeptide.

<3> Utilization of the Polypeptide and DNA of the Present Invention

The polypeptide of the present invention can be utilized for the synthesis of globo-series glycolipids, for example, for the synthesis of Gb3/CD77 by exposing the polypeptide of the present invention or a cultured product of the transformed cells trensfected with the DNA of the present invention to lactosylceramide, thereby evoking enzymatic reaction. Also, it is possible to obtain a glycolipid as represented by the following formula (1) by exposing the polypeptide of the present invention or a cultured product of the transformed cells transfected with the DNA of the present invention to galactosylceramide.

$$\text{Gal } \alpha1{\rightarrow}4\text{Gal-Cer} \tag{1}$$

In this procedure, exposure to substrate may occur through contact with the transformed cells, if the polypeptide of the present invention is produced and accumulated in the cytoplasm or in the membrane fraction, or through contact with medium if the polypeptide is accumulated in medium. When the cells in which the polypeptide of the present invention has been expressed are utilized, exposure to substrate may occur through direct contact with the cells themselves, or extracts therefrom, or immobilized extracts. The term "transformed cell" here includes not only transformed cells themselves but also extracts from them.

The polypeptide of the present invention is capable of specifically attaching a galactose residue to C4 position of galactose residue of lactosylceramide or galactosylceramide contained in a sugar chain of a glycoprotein. Further, the polypeptide of the present invention is utilized for selective synthesis of a sugar chain.

Although a number of members of β1,3-galactosyltransferases (β1,3Gal-Ts) or β1,4Gal-Ts have been identified(ref.27–30), this gene is the first and only α1,4Gal-T gene isolated so far. Moreover, no homologous genes to this gene were detected in the data base of *C. elegans* or *Drosophila melanogaster* genes, even though many β1,4 and β1,3Gal-T-related genes have been identified. These facts may indicate that α1,4Gal-T gene evolved relatively later than other galactosyltransferase genes, and globo-series glycolipids synthesized through Gb3 are playing more precise roles compared to glycolipids of the other series.

Gb3/CD77 seems to be unusual because it can mediate various apoptotic signals in both normal cells and malignant tumor cells, even though it does not contain any cytoplasmic domain(ref.16 and 31). The observed rapid death of CD77$^+$ BC B cells in vitro suggests that endogenous ligand molecules interact with Gb3/CD77 to bring about the physiologic selection of immature B cells(ref.11 and 32). Furthermore, the capability of B subunit of VT to induce apoptosis of Gb3/CD77$^+$ cells(ref.16) strongly encourages the investigation of Gb3/CD77-associating cytoplasmic molecules(ref.31). Investigations of these ligands and signal transducers relevant to Gb3/CD77 might contribute to further understanding of the B cell selection and of the pathogenesis of hemolytic uremic syndrome caused by *E.coli* O157 infection. In particular, the tissue specificity of the syndrome such as renal failure, hemolysis and neurological disorders, might be clarified by gene manipulation of the cloned Gb3/CD77 synthase.

Furthermore, it has recently been reported that Gb3/CD77 and ganglioside GM3 may function as alternative cofactors for the entry of human immunodeficiency virus type 1 (HIV-1) in CD4-induced interactions between gp120 and glycosphingolipid microdomains(ref.33 and 34). If this is the case, Gb3/CD77 may be a receptor not only for bacterial toxins but for viruses, and the regulation of Gb3/CD77 expression could be a key target for the therapeutic approaches of viral infections such as HIV-1.

Further, the expression of Gb3/CD77 in the kidney has been thought to be related with the development of hemolytic uremic syndrome (HUS). Furthermore, Fabry's disease is known as a disease in which Gb3/CD77 accumulates in the kidney, heart, brain and vasculature. From above, the polypeptide and DNA of the present invention, and the method of the present invention for producing Gb3/CD77 or a glycolipid may serve as a therapeutic tool, diagnostic tool or research tool for the treatment of diseases caused by the abnormal expression of Gb3/CD77 as described above.

EXAMPLE

The present invention will be described more in detail below by means of examples.

Example 1

Isolation of cDNA for α1,4-Galactosyltransferase (α1,4 Gal-T).

<1> Preparation of a cDNA Library from a Human Melanoma Cell Strain, and Cloning of α1,4 Gal-T cDNA.

A cDNA was prepared from poly(A$^+$) RNA of a human melanoma cell line SK-MEL-37 as described(ref.17). The cDNA library was constructed by inserting the cDNA into a vector plasmid pCDM8 (Invitrogen). The library contained 5×10$^6$ independent colonies. The strain of bacteria was *E. coli* MC1061/P3 (ref.18).

Since the SK-MEL-37 cell line does not express Gb3/CD77 on its surface, it highly efficiently expresses α1,4 Gal-T, and thus the cDNA library prepared from this cell line is excellent for the present purpose.

Plasmids of the cDNA library were transfected into a mouse fibroblast L cells together with pd13027 (polyoma T gene, provided by Dr. C. Basilico at New York University, New York) using DEAE-dextran as described (ref.18). L cells express a large amount of LacCer although they have no α1,4 Gal-T activity nor Gb3/CD77 expression(ref.19). The L cells, because of these characteristics, served as an excellent host in the cloning of cDNA for α1,4 Gal-T. The L cell was kindly provided by Dr. A. P. Albino at Sloan-Kettering Cancer Center, New York, and was maintained in Dulbecco's modified Eagle's minimal essential medium (DMEM) containing 7.5% of fetal bovine serum (FCS).

After 48 h, the transfected cells were detached and incubated with a rat monoclonal antibody (mAb) 38.13 (ref.6) on ice for 45 min. After washing, cells were plated on dishes coated with rabbit anti-rat IgM (ZYMED) as described (ref.17). Plasmid DNA was rescued from the panned cells by preparing Hirt extracts, and transformed into MC161/P3. The same procedure was repeated 5 times. The plasmid DNA was collected from the transformed cells.

Using microscale transfection of L cell and immunofluorescence assay, cDNA clones that determined the Gb3/CD77 expression were isolated. Cell surface expression of Gb3/CD77 was analyzed by flow cytometry (Becton Dickinson) as described(ref.19). MAbs 38.13 or TU-1 (23) were used with FITC-conjugated rabbit anti-rat IgG or anti-mouse IgM (ZYMED), respectively. As a result, two clones showing positive reactions were successfully isolated. As described later, the two clones are essentially similar in nature, and thus one of them is called pVTR1, and further analysis was performed on that one.

Figure 1:
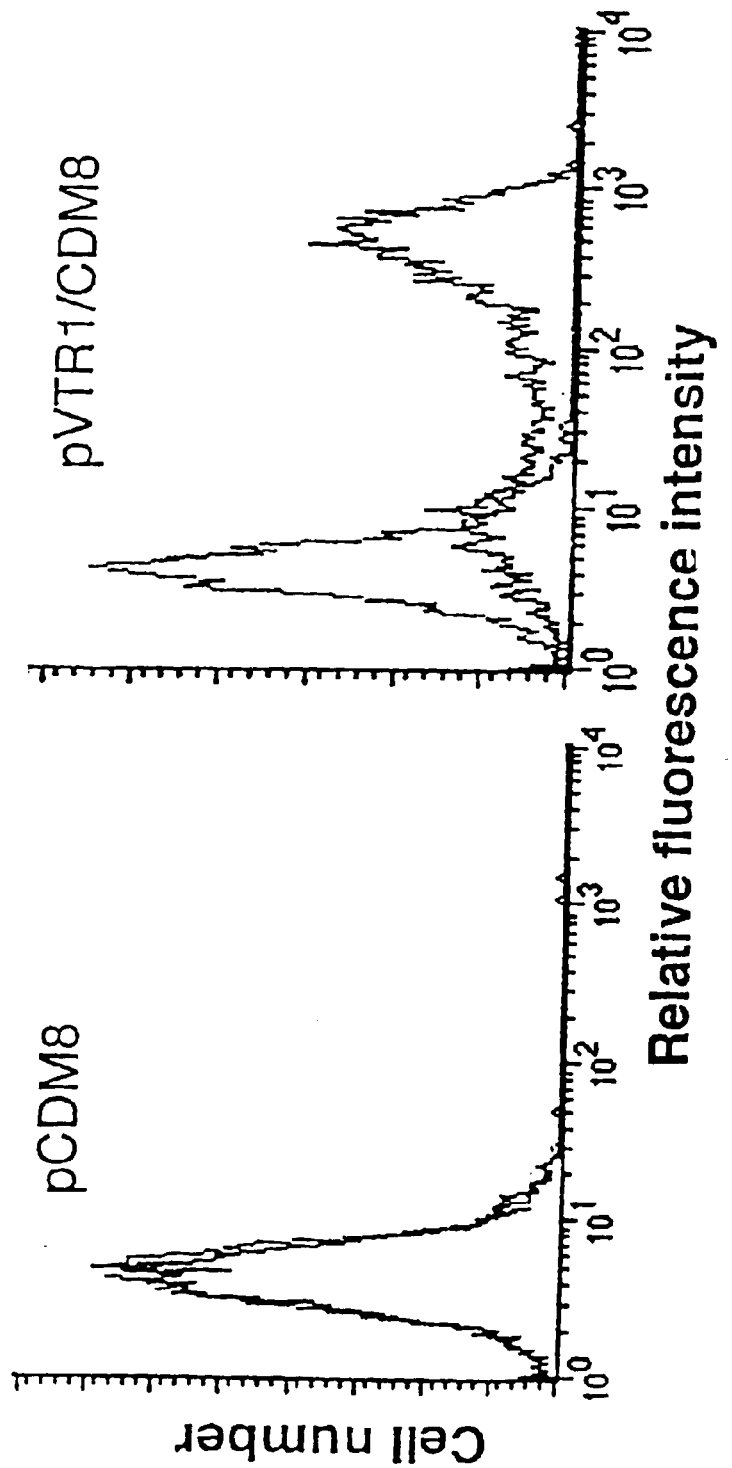
FIG. 1 shows flow cytometry indicating the expression of Gb3/CD77 by L cells. The left diagram relates to L cells transfected with pCDM8 while the right diagram to L cells transfected with pVTR1/CDM8. The thick line indicates the result of cells stained with mAb38.13 and FITC-conjugated rabbit anti-rat IgG (secondary antibodies) while the thin line the result of cells stained only with the secondary antibodies (control).

FIG. 1 shows the results of flow cytometry of L cells transfected with the plasmid pVTR1 or the plasmid pCDM8

(containing no target sequence to serve as control). It is obvious from this that the cells transfected with pVTR1 express Gb3/CD77 while those transfected with pCDM8 alone do not express Gb3/CD77. It was thus demonstrated that α1,4 Gal-T cDNA inserted to pVTR1 is involved in the synthesis of Gb3/CD77.

<2> Extraction of Glycolipids from the Transformed Cells, and Identification of Gb3/CD77

Glycolipids were extracted as described(ref.21). Briefly, glycolipids were extracted from about 400 μl of packed cells using chloroform/methanol (2:1, 1:1, 1:2) sequentially. TLC was performed on a high performance TLC plates (MERCK, Darmstadt) using the solvent system chloroform:methanol: 0.22% $CaCl_2$ (60:35:8) and sprayed by orcinol. For standards, bovine brain ganglioside mixture (Wako, Tokyo), neutral glycolipids from human erythrocytes, and Gb3 (Sigma) were used.

Glycosphingolipids extracted from the transformed cells showed definite Gb3 bands in TLC, although the transformed cells with pCDM8 alone showed no Gb3 band (FIG. 2A), suggesting that the cloned pVTR1derived from α1,4Gal-T gene.

Figure 2:
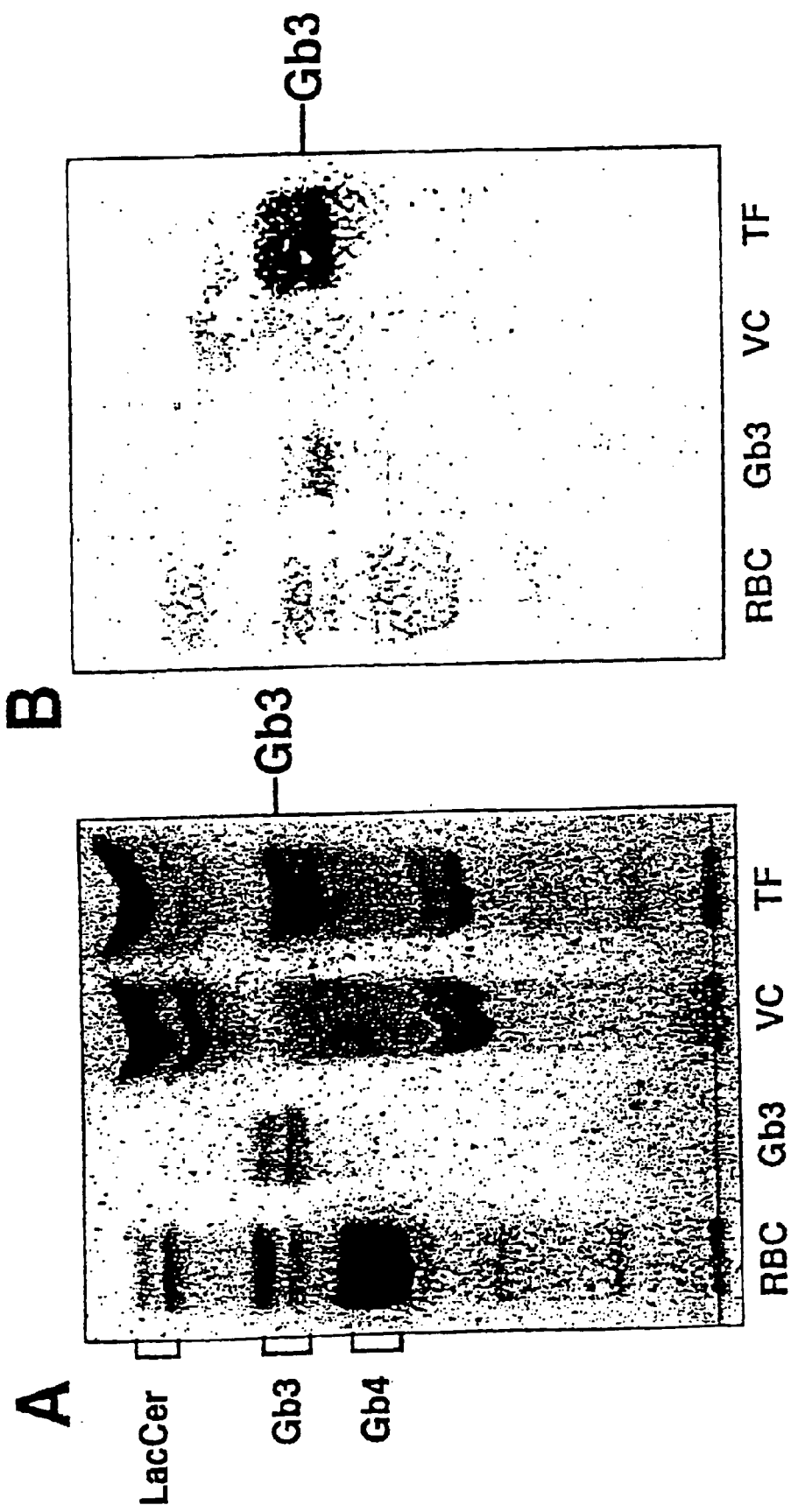
FIG. 2 shows TLC charts of glycolipids extracted from cells transiently transfected with α1,4 Gal-T gene.

The identity of Gb3/CD77 was confirmed by TLC-immunostaining using an aluminum-backed silica plate (MERCK) as described(ref.21). After TLC, the plate was blotted onto PVDF membrane as described(ref.22). After blocking, the plate was incubated with mAb, then antibody binding was detected with ABC kit (vector Laboratories, Burlingame, Calif.) and Konica Immunostaining HRP-1000 (Konica, Tokyo). This TLC-immunostaining revealed strong bands of Gb3 only in the extracts from the cDNA transfected cells (FIG. 2B).

<3> Nucleotide Sequencing of Gene for α1,4 Gal-T

The nucleotide sequence of the cDNA clone which was confirmed to express Gb3/CD77 as described above was determined by dideoxynucleotide termination sequencing using the PRISM dye terminator cycle sequencing kit and model 310 DNA sequencer (Applied Biosystems). The sequencing showed that the two clones are essentially the same in sequence. Accordingly, one of them was selected for subsequent analysis, and named pVTR1. The nucleotide sequence of cDNA in pVTR1 is shown by SEQ ID NO:1. The amino acid sequence encoded by this nucleotide sequence is shown by SEQ ID NOs:1 and 2.

The initiation codon is embedded within a sequence similar to the Kozak consensus initiation sequence(ref. 24 and 25). This open reading frame predicts a 353-amino acid protein with a molecular mass of 40,498 daltons.

Nucleotide and amino acid sequence homology search was carried out using the internet program BLAST (National Center for Biotechnology Information). However, no cDNA or protein having a high homology with these sequences was found in the database.

Amino acid sequence and hydropathy analyses (35) were performed with a software GENETYX-MAC version 8.0 (Software Development, Tokyo)(FIG. 3). A single hydrophobic segment with 26 amino acids was present near the amino terminus (amino acid Nos. 20–45 in SEQ ID NO: 2). This putative signal anchor sequence would place 19 residues within the cytoplasm and 308 amino acids within the Golgi lumen.

The presence of two potential N-glycosylation sites are indicated (amino acid sequence Nos. 121–123 and 203–205 in SEQ ID NO: 2). Relatively high frequency of proline (10/31) was detected at the C'-side of the transmembrane domain.

Example 2

Characterization and Production of α1,4 Gal-T

<1> Enzyme Assay of α1,4 Gal-T

Membrane fractions were prepared as described(ref.19) from L cells transfected with the gene for α1,4 Gal-T as obtained in Example 1. The enzyme activity of α1,4 Gal-T in the membrane fraction was measured as descibed previously(ref.4). The reaction mixture for the assay contained the following in a volume of 50 μl:50 mM sodium cacodylate-HCl (pH 6.0), 10 mM $MgCl_2$, 5 mM galactonolactone (Sigma), 0.3% Triton X-100 (Sigma), 0.4 mM (LacCer), 2.9 mM phosphatidylglycerol (Sigma), 0.2 mM UDP-Gal (Sigma), UDP-[$^{14}C$] Gal ($2.5 \times 10^5$ dpm) (NEN), and membrane fraction containing 50 μg protein. The protein concentration was determined by Lowry's methods (ref.20). The products was isolated by a $C_{18}$ Sep-Pak cartridge (Waters, Milford, Mass.) and analyzed by thin layer chromatography (TLC) and autoradiography using a Bio-Imaging Analyzer BAS2000 (Fuji Film, Tokyo). The results are shown in FIG. 4A.

L cells transfected with pVTR1/CDM8 showed high Gb3 synthase activity (7,012 units, pmol/h/mg of protein) when LacCer was used as an acceptor. On the other hand, L cells transfected with pCDM8 alone were completely negative. Thus, this cDNA determined α1,4Gal-T activity and the surface expression of Gb3/CD77, indicating that this cDNA encodes the Gb3/CD77 synthase.

Enzyme activity toward other potential acceptors was also examined (FIG. 4B). None of the acceptors examined except LacCer and galactosylceramide showed significant levels of [$^{14}C$] galactose incorporation (FIG. 4B). Km values for these two substrates were 54.5 μM (LacCer) and 132 μM (galactosylceramide). The P1 antigen in the P blood group system is also formed by α1,4 galactose transfer (acting on paragloboside(PG)), but it was confirmed that this enzyme is not responsible for the synthesis of P1 antigen (FIG. 4B).

Example 3

Expression Analysis of α1,4 Gal-T Gene in Various Tissues (Northern Blotting)

Multiple Choice Northern Blots menbranes (OriGene Technologies, Rockville, Mass.) were used. They were hybridized with [$^{32}P$]dCTP-labeled cDNA probe of pVTR1 or control β-actin as described (ref.18 and 19). The relative expression levels of mRNA of α1,4Gal-T gene among human tissues measured by Bio-Imaging Analyzer BAS2000 (Fuji Film) are presented as a percentage of the value of heart after correction with the control. Expression levels of the α1,4Gal-T gene in various human tissues were examined by Northern blotting. Among tissues examined, heart, kidney, spleen, liver, testis and placenta strongly expressed the gene (FIG. 5).

Example 4

Stable Transfection of Cells with pVTR1 Plasmid

To prepare stable transformants, pVTR1 and pSV2neo were co-transfected into L cells using Lipofection kit (TOYOBO, Tokyo, Japan). To select transformants, the cells were cultured in DMEM containing FCS (7.5%) and G418 (300 μg/ml). G481 is inactivated by 3'-O-aminoglycoside phosphotransferase encoded by the neo gene.

G418-resistant cells were cloned by limiting dilution. Clones transfected with pSV2neo alone were prepared for control. These cells were incubated together with mAb38.13, followed by addition of FITC-conjugated rabbit anti-rat IgG for reaction, and the resulting cells were subjected to flow cytometry in the same manner as described above. The results showed that the cells transfected with pVTR1 and pSV2neo(L-VTR1) strongly expressed Gb3/CD77 while those transfected with pSV2neo alone(L-neo) did not express Gb3/CD77 (FIG. 6).

Example 5

Reaction of Transformed Cells to Verotoxins

<1> MTT Assay

To compare the reactions of L-VTR1 and L-neo to VTs, MTT assay was performed using cells prepared in 48 well plates ($1\times10^4$ cells/well) and cultured in the presence of VT1or VT2. The assay was performed by triplicated samples. To quantify the cell proliferation, 50 µl of 5 mg/ml of MTT (Sigma) in PBS was added to each well.

After incubation for 5 h at 37° C., the supernatants were aspirated and 100 µl of n-propylalchohol containing 0.1% NP40 and 4 mM HCl was added. The color reaction was quantitated using automatic plate reader IMMUNO-MINI NJ-2300 (Nihon InterMed, Tokyo, Japan) at 590 nm with a reference filter of 620 nm.

L-VTR1 in VT (+) medium showed marked growth suppression compared to that cultured in the absence of VT, while L-neo showed no effects of VT (FIG. 7). MTT assay of L-VTR1 and L-neo after the exposure to various concentrations of VTs revealed marked growth suppression of L-VTR1 even at 0.01 ng/ml, but not of L-neo (FIG. 8).

<2> DNA Fragmentation Assay

DNA fragmentation assay was performed to determine the mechanism responsible for the death of L-VTR1 treated with VTs. Cells were cultured in the presence of VT2 (200 ng/ml). After 24 h, cells were collected and the pellets were lysed in 100 µl of lysis buffer (10 mM Tris-HCl pH 7.4, 10 mM EDTA and 0.5% Triton X-100) for 10 min at 4° C. After centrifugation, the supernatants were collected, and 2 µl of RNAse (10 mg/ml) and 2 µl of Proteinase K (10 mg/ml) were added. After incubation for 1 h at 37° C., the fragmented DNA was 2-propanol precipitated. Electrophoresis was conducted using DNA derived from $1.5\times10^6$ cells in 2% agarose gel containing 0.2 µg/ml ethidium bromide in TEA buffer.

Agarose gel electrophoresis of cytoplasmic DNA extracted from L-VTR1 revealed a clear pattern of DNA fragmentation characteristic of apoptosis (FIG. 9). In contrast, the L-neo sample did not show any ladder formation. Thus, it was confirmed that Gb3 /CD77 generated by the cDNA serves as a functional receptor for VTs.

The present invention provides α1,4-galactosyltransferase, and DNA encoding thereof. That enzyme can be utilized for the production of globo-series glycolipids such as Gb3/CD77.

Further, the DNA is useful for production of the above described enzyme, or serves as a therapeutic tool, diagnostic tool or research tool for the treatment of diseases caused by the abnormal expression of Gb3/CD77, or it may be useful for the treatment or diagnosis of diseases involved in the action of verotoxins.

References

1. Wiegandt, H. (ed)(1985) in Glycolipids, pp. 199–260, Elsevier Science Publishing Co., Inc., New York
2. Paulson, J. C., and Colley, K. J. (1989) J. Biol. Chem. 264,17615–17618
3. Lloyd, K. O., and Furukawa, K. (199B) Glycoconj. J. 15, 627–636
4. Taga, S., Mangeney, M., Tursz, T., and Wiels, J. (1995) Int. J. Cancer 61, 261–267
5. Marcus, D. M., Kundu, S. K., and Suzuki, A. (1981) Seminars in Haematology, 18, 63–71
6. Wiels, J., Fellous, M., and Tursz, T. (1981) Proc. Natl. Acad. Sci. USA 78, 6485–6488
7. Klein, G., Manneborg-Sandlund, A., Ehlin-Henriksson, B., Godal, T., Wiels, J., and Tursz, T. (1983) Int. J. Cancer 31, 535–542
8. Balana, A., Wiels, J., Tetaud, C., Mishal, Z., Tursz, T. (1985) Int. J. Cancer 36, 453–460
9. Murray, L. J., Habeshaw, J. A., Wiels, J., and Greaves, M. F. (1985) Int. J. Cancer 36, 453–460
10. Knapp, W. et al.(Eds) (1989) in Leukocyte typing IV, p. 118, Oxford University Press
11. Mangeney, M., Richard, Y., Coulaud, D., Tursz, T., and Wiels, J. (1991) Eur. J. Immunol. 21, 1131–1140
12. Gregory, C. D., Dive, C., Henderson, S., Smith, C. A., Williams, G. T., Gordon, J., and Rickinson, A. B. (1991) Nature 349, 612–614
13. O'Brien, A. D., Lively, T. A., Chen, M. E., Rothman, S. W., and Formal, S. B. (1983) Lancet, 1, 702
14. Lingwood, C. A., Law, H., Richardson, S., Petric, M., Brunton, J. L., De Grandis, S., and Karmali, M. (1987) J. Biol. Chem. 262,8834–8839
15. Endo, Y., Tsurugi, K., Yutsudo, T., Takeda, Y., Ogasawara, T., and Igarashi, K. (1988) Eur. J. Biochem. 171, 45–50.
16. Mangeney, M., Lingwood, C. A., Taga, S., Caillou, B., Tursz, T., and Wiels, J. (1993) Cancer Res. 53, 5314–5319
17. Seed B, Aruffo A (1987) Proc. Natl. Acad. Sci. USA 84, 3365–3369
18. Nagata, Y., Yamashiro, S., Yodoi, J., Lloyd, K. O., Shiku, H., and Furukawa, K. (1992) J. Biol. Chem. 267, 12082–12089
19. Yamashiro, S., Haraguchi, M., Furukawa, K., Takamiya, K., Yamamoto, A., Nagata, Y., Lloyd, K. O., Shiku, H., and Furukawa, K. (1995) J. Biol. Chem. 270, 6149–6155
20. Lowry, O. H., Rosenbrough, N. J., Parr, A. L., and Randall, R. J. (1951) J. Biol. Chem. 193, 265–275
21. Furukawa, K., Clausen, H., Hakomori, S., Sakamoto, J., Look, K., Lundblad, A., Mattes, M. J., and Lloyd, K. O. (1985) Biochemistry 24, 7820–7826
22. Taki, T., Handa, S., and Ishikawa, D. (1994) Anal. Biochem. 221, 312–316
23. Miyamoto, D., Ueno, T., Takashima, S., Ohta, K., Miyawaki, T., Suzuki, T., and Suzuki, Y. (1997) Glycoconj. J. 14, 379–388
24. Kozak, M. (1986) Cell 44, 283–292
25. Kozak, M. (1989) J. Cell Biol. 108, 229–241
26. Wiels, J., Holmes, E. H., Cochran, N., Tursz, T., and Hakomori, S. (1984) J. Biol. Chem. 259, 14783–14787
27. Amado, M., Almeida, R., Carneiro, F., Levery, S. B., Holmes, E. H., Nomoto, M., Hollingsworth, M. A., Hassan, H., Schwientek, T., Nielsen, P. A., Bennett, E. P., and Clausen, H. (1998) J. Biol. Chem. 273, 12770–12778
28. Schwientek, T., Almeida, R., Levery, S. B., Holmes, E. H., Bennett E, and Clausen, H. (1998) J Biol Chem. 273, 29331–29340.
29. Almeida, R., Amado, M., David, L., Levery, S. B., Holmes, E. H., Merkx, G., van Kessel, A. G., Rygaard, E., Hassan, H., Bennett, E., and Clausen, H. (1997) J. Biol. Chem. 272, 31979–31991
30. Lo, N. W., Shaper, J. H., Pevsner, J., and Shaper, N. L. (1998) Glycobiology 8, 517–526

31. Taga, S., Carlier, K., Mishal, Z., Capoulade, C., Mangeney, M., Lecluse, Y., Coulaud, D., Tetaud, C., Pritchard, L. L., Tursz, T., and Wiels, J. (1997) Blood 90, 2757–2767
32. Mangeney, M., Rousselet, G., Taga, S., Tursz, T., and Wiels, J. (1995) Mol. Immunol. 32, 333–339
33. Puri, A., Hug, P., Jernigan, K., Barchi, J., Kim, H.-Y., Hamilton, J., Wiels, J., Murray, G. J., Brady, R. O., and Blumenthal, R. (1998) Proc. Natl. Acad. Sci. USA 95, 14435–14440
34. Hammache, D., Yahi, N., Maresca, M., Pieroni, G., and Fantini, J. (1999) J. Virol. 73, 5244–5248
35. Kyte, J., and Doolittle, R. F. (1982) J. Mol. Biol. 157, 105–132
36. Svennerholm, L. (1963) J. Neurochem. 10, 613–623

What is claimed is:

1. An isolated DNA consisting essentially of SEQ ID NO:1.

2. A vector comprising the isolated DNA of claim 1.

3. A cell transformed with the isolated DNA of claim 1.

4. A method of producing an α1,4-galactosyltransferase, comprising culturing the cell of claim 3 in a medium suitable for expressing the α1,4-galactosyltransferase; and recovering the α1,4-galactosyltransferase from one or both of the medium and cell extract of the cell.

* * * * *

SEQUENCE LISTING

```
<160> NUMBER OF SEQ ID NOS: 2

<210> SEQ ID NO 1
<211> LENGTH: 1975
<212> TYPE: DNA
<213> ORGANISM: Homo sapiens
<220> FEATURE:
<221> NAME/KEY: CDS
<222> LOCATION: (134)..(1192)
<223> OTHER INFORMATION:

<400> SEQUENCE: 1 aagtcggct gctgagccag ggcgtgtctc ccggaggcct gtgggctgcc aggatcccca      60
cctctctgca atgggctgcc caggctgacc agccggttcc tgctggaagc tcctggtctg    120
atctggggat acc atg tcc aag ccc ccc gac ctc ctg ctg cgg ctg ctc      169
            Met Ser Lys Pro Pro Asp Leu Leu Leu Arg Leu Leu
              1               5                  10 cgg ggc gcc cca agg cag cgg gtc tgc acc ctg ttc atc atc ggc ttc    217
Arg Gly Ala Pro Arg Gln Arg Val Cys Thr Leu Phe Ile Ile Gly Phe
         15                  20                  25 aag ttc acg ttt ttc gtc tcc atc atg atc tac tgg cac gtt gtg gga    265
Lys Phe Thr Phe Phe Val Ser Ile Met Ile Tyr Trp His Val Val Gly
     30                  35                  40 gag ccc aag gag aaa ggg cag ctc tat aac ctg cca gca gag atc ccc    313
Glu Pro Lys Glu Lys Gly Gln Leu Tyr Asn Leu Pro Ala Glu Ile Pro
 45                  50                  55                  60 tgc ccc acc ttg aca ccc ccc acc cca ccc tcc cac ggc ccc act cca    361
Cys Pro Thr Leu Thr Pro Pro Thr Pro Pro Ser His Gly Pro Thr Pro
                 65                  70                  75 ggc aac atc ttc ttc ctg gag act tca gac cgg acc aac ccc aac ttc    409
Gly Asn Ile Phe Phe Leu Glu Thr Ser Asp Arg Thr Asn Pro Asn Phe
             80                  85                  90 ctg ttc atg tgc tcg gtg gag tcg gcc gcc aga act cac ccc gaa tcc    457
Leu Phe Met Cys Ser Val Glu Ser Ala Ala Arg Thr His Pro Glu Ser
         95                 100                 105 cac gtg ctg gtc ctg atg aaa ggg ctt ccg ggt ggc aac gcc tct ctg    505
His Val Leu Val Leu Met Lys Gly Leu Pro Gly Gly Asn Ala Ser Leu
    110                 115                 120 ccc cgg cac ctg ggc atc tca ctt ctg agc tgc ttc ccg aat gtc cag    553
Pro Arg His Leu Gly Ile Ser Leu Leu Ser Cys Phe Pro Asn Val Gln
125                 130                 135                 140 atg ctc ccg ctg gac ctg cgg gag ctg ttc cgg gac aca ccc ctg gcc    601
Met Leu Pro Leu Asp Leu Arg Glu Leu Phe Arg Asp Thr Pro Leu Ala
                145                 150                 155 gac tgg tac gcg gcc gtg cag ggg cgc tgg gag ccc tac ctg ctg ccc    649
Asp Trp Tyr Ala Ala Val Gln Gly Arg Trp Glu Pro Tyr Leu Leu Pro
            160                 165                 170 gtg ctc tcc gac gcc tcc agg atc gca ctc atg tgg aag ttc ggc ggc    697
Val Leu Ser Asp Ala Ser Arg Ile Ala Leu Met Trp Lys Phe Gly Gly
        175                 180                 185
```

| | | |
|---|---|---|
| atc tac ctg gac acg gac ttc att gtt ctc aag aac ctg cgg aac ctg<br>Ile Tyr Leu Asp Thr Asp Phe Ile Val Leu Lys Asn Leu Arg Asn Leu<br>    190                 195                 200 | | 745 |
| acc aac gtg ctg ggc acc cag tcc cgc tac gtc ctc aac ggc gcg ttc<br>Thr Asn Val Leu Gly Thr Gln Ser Arg Tyr Val Leu Asn Gly Ala Phe<br>205                 210                 215                 220 | | 793 |
| ctg gcc ttc gag cgc cgg cac gag ttc atg gcg ctg tgc atg cgg gac<br>Leu Ala Phe Glu Arg Arg His Glu Phe Met Ala Leu Cys Met Arg Asp<br>                    225                 230                 235 | | 841 |
| ttc gtg gac cac tac aac ggc tgg atc tgg ggt cac cag ggc ccg cag<br>Phe Val Asp His Tyr Asn Gly Trp Ile Trp Gly His Gln Gly Pro Gln<br>                        240                 245                 250 | | 889 |
| ctg ctc acg cgg gtc ttc aag aag tgg tgt tcc atc cgc agc ctg gcc<br>Leu Leu Thr Arg Val Phe Lys Lys Trp Cys Ser Ile Arg Ser Leu Ala<br>                            255                 260                 265 | | 937 |
| gag agc cgc gcc tgc cgc ggc gtc acc acc ctg ccc cct gag gcc ttc<br>Glu Ser Arg Ala Cys Arg Gly Val Thr Thr Leu Pro Pro Glu Ala Phe<br>                    270                 275                 280 | | 985 |
| tac ccc atc ccc tgg cag gac tgg aag aag tac ttt gag gac atc aac<br>Tyr Pro Ile Pro Trp Gln Asp Trp Lys Lys Tyr Phe Glu Asp Ile Asn<br>285                 290                 295                 300 | | 1033 |
| ccg gag gag ctg ccg cgg ctg ctc agt gcc acc tat gct gtc cac gtg<br>Pro Glu Glu Leu Pro Arg Leu Leu Ser Ala Thr Tyr Ala Val His Val<br>                        305                 310                 315 | | 1081 |
| tgg aac aag aag agc cag ggc acg cgg ttc gag gcc acg tcc agg gca<br>Trp Asn Lys Lys Ser Gln Gly Thr Arg Phe Glu Ala Thr Ser Arg Ala<br>                    320                 325                 330 | | 1129 |
| ctg ctg gcc cag ctg cat gcc cgc tac tgc ccc acg acg cac gag gcc<br>Leu Leu Ala Gln Leu His Ala Arg Tyr Cys Pro Thr Thr His Glu Ala<br>                335                 340                 345 | | 1177 |
| atg aaa atg tac ttg tgaggggccc gccaggtcac ctccccaacc tgctcctgat<br>Met Lys Met Tyr Leu<br>            350 | | 1232 |
| ggggcactgg gccgcccttc ccggggaggc aagattgagg gcccgggaga gggaggcccg | | 1292 |
| agctgccacc gggcttaggc aggctgttga ggagctgtgg gagcaggccc agtgggaggc | | 1352 |
| tgtggacacc ccgaggacag tgtcctgtct cgaggcaggg ctgacacatg gtgccatagc | | 1412 |
| cagcggaggg cgctcagtga gtgccccggg ccttctagac aacaggcagg aaggatgaac | | 1472 |
| ctcagggcac cccaggtgg tgcggaaagc caggcagttg ggacagaggt gcccacgagg | | 1532 |
| gcagaggccg gtgctaaggg gatggggaag aagggacaag attcccagag aggagaggag | | 1592 |
| gctgttggta ggaaagtggc agggctgggg gagacccagc cccaagggtc cggggcggag | | 1652 |
| gatgctttgt tcttttctgg ttttggttcc tctttcgcgg ggggtggggg aggtcaacag | | 1712 |
| ggactgagtg gggcagaggc ccagaagtgc cagcctgggg agccgtttgg gggcagcccc | | 1772 |
| ttctgcccac cccatccttc ttcctctcca gagatgccag gggggcgtgt atgctctgcc | | 1832 |
| ccttccctca gacaggggct gggtggggag gctcttaggg ctcaggagaa gcattttaaa | | 1892 |
| gaaaccccca ccctgccgcc cgcattataa acacaggaga ataatcaata gaataaaagt | | 1952 |
| gaccgactgt caaaaaaaaa aaa | | 1975 |

<210> SEQ ID NO 2
<211> LENGTH: 353
<212> TYPE: PRT
<213> ORGANISM: Homo sapiens

<400> SEQUENCE: 2

Met Ser Lys Pro Pro Asp Leu Leu Leu Arg Leu Leu Arg Gly Ala Pro

-continued

```
  1               5              10              15
Arg Gln Arg Val Cys Thr Leu Phe Ile Ile Gly Phe Lys Phe Thr Phe
            20              25              30

Phe Val Ser Ile Met Ile Tyr Trp His Val Val Gly Glu Pro Lys Glu
            35              40              45

Lys Gly Gln Leu Tyr Asn Leu Pro Ala Glu Ile Pro Cys Pro Thr Leu
            50              55              60

Thr Pro Pro Thr Pro Pro Ser His Gly Pro Thr Pro Gly Asn Ile Phe
 65             70              75              80

Phe Leu Glu Thr Ser Asp Arg Thr Asn Pro Asn Phe Leu Phe Met Cys
            85              90              95

Ser Val Glu Ser Ala Ala Arg Thr His Pro Glu Ser His Val Leu Val
            100             105             110

Leu Met Lys Gly Leu Pro Gly Gly Asn Ala Ser Leu Pro Arg His Leu
            115             120             125

Gly Ile Ser Leu Leu Ser Cys Phe Pro Asn Val Gln Met Leu Pro Leu
 130            135             140

Asp Leu Arg Glu Leu Phe Arg Asp Thr Pro Leu Ala Asp Trp Tyr Ala
145             150             155             160

Ala Val Gln Gly Arg Trp Glu Pro Tyr Leu Leu Pro Val Leu Ser Asp
            165             170             175

Ala Ser Arg Ile Ala Leu Met Trp Lys Phe Gly Gly Ile Tyr Leu Asp
            180             185             190

Thr Asp Phe Ile Val Leu Lys Asn Leu Arg Asn Leu Thr Asn Val Leu
            195             200             205

Gly Thr Gln Ser Arg Tyr Val Leu Asn Gly Ala Phe Leu Ala Phe Glu
 210            215             220

Arg Arg His Glu Phe Met Ala Leu Cys Met Arg Asp Phe Val Asp His
225             230             235             240

Tyr Asn Gly Trp Ile Trp Gly His Gln Gly Pro Gln Leu Leu Thr Arg
            245             250             255

Val Phe Lys Lys Trp Cys Ser Ile Arg Ser Leu Ala Glu Ser Arg Ala
            260             265             270

Cys Arg Gly Val Thr Thr Leu Pro Pro Glu Ala Phe Tyr Pro Ile Pro
            275             280             285

Trp Gln Asp Trp Lys Lys Tyr Phe Glu Asp Ile Asn Pro Glu Glu Leu
            290             295             300

Pro Arg Leu Leu Ser Ala Thr Tyr Ala Val His Val Trp Asn Lys Lys
305             310             315             320

Ser Gln Gly Thr Arg Phe Glu Ala Thr Ser Arg Ala Leu Leu Ala Gln
            325             330             335

Leu His Ala Arg Tyr Cys Pro Thr Thr His Glu Ala Met Lys Met Tyr
            340             345             350

Leu
```